United States Patent
Schisler et al.

(10) Patent No.: US 6,562,337 B2
(45) Date of Patent: May 13, 2003

(54) YEASTS FOR REDUCING FUSARIUM HEAD BLIGHT IN CEREALS AND SELECTION THEREOF

(75) Inventors: David A. Schisler, Morton, IL (US); Naseem I. Khan, Peoria, IL (US); Michael J. Boehm, Worthington, OH (US)

(73) Assignees: The United States of America as represented by the Secretary of Agriculture, Washington, DC (US); The Ohio State University Research, Columbus, OH (US)

( * ) Notice: Subject to any disclaimer, the term of this patent is extended or adjusted under 35 U.S.C. 154(b) by 47 days.

(21) Appl. No.: 09/864,639

(22) Filed: May 24, 2001

(65) Prior Publication Data

US 2001/0041176 A1 Nov. 15, 2001

Related U.S. Application Data

(63) Continuation-in-part of application No. 09/414,200, filed on Oct. 7, 1999, now abandoned.
(51) Int. Cl.$^7$ ............................................... A01N 63/04
(52) U.S. Cl. ............................... 424/93.51; 435/255.1; 435/252.5; 424/93.46; 504/117
(58) Field of Search ........................ 424/93.51, 93.46; 435/255.1, 252.5; 504/117

(56) References Cited

PUBLICATIONS

N. I. Khan et al., "Developing strategies and organisms for biocontrol of head scab of wheat", Phytopathology 88:S47 (1998).*

N. I. Khan et al., "Biological control of scab of wheat incited by *Gibberella zeae*", proceedings of the 1998 National Fusarium Head Blight Forum, Michigan State University, East Lansing, MI, pp 45–46, Oct. 26–27, 1998.*
N. I. Khan et al., "Performance of selected antagonists of Fusarium head blight against a range of *Gibberella zeae* isolates", Phytopathology 89:S39 (1999).*
D. A. Schisler et al., "Selection and evaluation of microbial antagonists active against *Gibberella zeae*, a casual agent of Fusarium head blight in wheat", proceedings of the 99$^{th}$ General Meeting of the American Society of Microbiology, pp. 575 (1999).*
W. C. da Luz et al., "Biocontrol of fungal pathogens of wheat with bacteria and yeasts", proceedings of the 5$^{th}$ International Congress of Plant Pathology, Kyoto Japan, pp. 2–134, Aug. 20–27, 1988.*
W. C. da Luz et al., "Seed microbiolization for control of Fusarium species in cereals", Phytopathology 87:S22 (1997).*
C. M. Stockwell et al., "Biocontrol of wheat scab with microbial antagonists", Phytopathology 87:S94 (1997).*
N. L. Perondi et al., "Controle Microbiologico Da Giberla Do Trigo", Fitopatol. Bras. vol. 21, No. 2, pp. 243–249 (1996).*
ATCC Catalogue of Yeasts, pp. 66–69 (1995).*

* cited by examiner

*Primary Examiner*—Irene Marx
(74) *Attorney, Agent, or Firm*—John D. Fado; Curtis P. Ribando

(57) ABSTRACT

Four yeasts (NRRL Y-30213, NRRL Y-30214, NRRL Y-30215, and NRRL Y-30216) and 1 bacterium (NRRL B-30212) have been identified as being superior antagonists capable of suppressing Fusarium head blight (head scab) in cereals, particularly in wheat and barley. Fusarium head blight is primarily caused by the fungus *Gibberella zeae* (anamorph=*Fusarium graminearum*).

11 Claims, No Drawings

YEASTS FOR REDUCING FUSARIUM HEAD BLIGHT IN CEREALS AND SELECTION THEREOF

This application is a continuation-in-part of application Ser. No. 09/414,200, filed Oct. 7, 1999 now abandoned.

BACKGROUND OF THE INVENTION

1. Field of the Invention

Head scab, also known as Fusarium head blight (FHB), is a devastating disease of wheat and barley that is primarily caused by the fungus Gibberella zeae (anamorph=*Fusarium graminearum*). This disease can reach epidemic levels and causes extensive damage to wheat and barley in humid and semi-humid wheat growing areas of the world. In recent growing seasons, the disease has caused large scale devastation in the United States, Canada and China. FHB was responsible for almost 500 million bushels of wheat lost in the United States from 1991 until present. Economic loss has been estimated at between 1.3 to 2.6 billion during this time period. In an epidemic in Indiana in 1986, grain samples from 43 of 44 counties had scab [Tuite et al., (1990) *Plant Dis.* 74:959–962]. Other countries of the world that produce large amounts of wheat in humid and semi-humid regions and would be susceptible to major outbreaks of FHB include India, Russia, France, Germany and the United Kingdom.

The infection of seed by G. zeae reduces seed germination, seedling vigor and plant emergence [Bechtel et al., (1985) *Cereal Chem.* 62:191–197]. Infection of wheat kernels by G. zeae reduces grain yield and affects grain quality [Clear et al., (1990) *Can. J. Plant Sci.* 70:1057–1069]. Reductions in grain yield are at least partially attributable to the pathogen producing the vomitoxin deoxynivalenol (DON) [Snijders, (1990) *Neth J. Plant Pathol.* 96:187–198; Proctor et al., (1995) *MPMI* 8:593–601] which can inhibit amino acid incorporation and protein production in plant tissues [Casale et al., (1988) *Phytopathology* 78:1673–1677]. This toxin is also implicated in adversely affecting the growth of mammalian cells [Knasmüller et al., (1997) *Mutation Research* 391:39–48]. DON is retained in semolina at approximately 50% and *F. graminearum* has a strong adverse effect on pasta color when Fusarium damaged kernels make up as little as 2% of a lot [Dexter et al., (1997) *Cereal Chem.* 74:519–525]. Additionally, G. zeae infected kernels can contain the estrogenic toxin zearalenone. Grain contaminated with either of these mycotoxins often is downgraded or can not be sold [Tuite et al., (1990)]. Contaminated grain is frequently unsuitable for human consumption and may be refused as feed [Vesonder et al., (1980) *Process Biochem.* 16:12–15]. The importance of FHB was recognized by the 105th U.S. Congress when it adopted the "Wheat and Barley Protection Act" that authorized expenditure of 26 million dollars for the study of FHB.

This invention relates to five microbial antagonists that reduce FHB.

2. Description of the Prior Art

Though some success in controlling FHB can be expected by plowing fields to bury crop residues infested with *F. graminearum* after harvest [Bai et al., (1994) *Plant Dis.* 78:760–766], minimal tillage practices render this alternative unacceptable. Some progress has been made in finding and analyzing scab resistance in wheat, though all cultivars in current production are susceptible [Bai et al., (1994)]. Foliar fungicides applied at anthesis can be useful in reducing scab [McMullen, (1998) Fungicide technology network of the National FHB initiative—1998 Report. Proceedings of the 1998 Head Scab Forum, Michigan State University, October 26–27, pp.47–49], but few fungicides are registered for use on wheat this late in the growing season [Shaner et al., (1992) *Fungic. Nematicide Tests.* 47:206–207]. Additionally, costs and concerns in the public and private sectors over pesticide residues in the environment and in food products render this disease control alternative less attractive.

Biological control, though currently not available, would be an environmentally acceptable method for substantially decreasing the level of disease incited by G. zeae. Though biological control agents (BCA's) have become a more acceptable control alternative for plant pathogens and BCA products are being marketed to a greater extent than ever before [Fravel et al., (1996) *Biological and Cultural Tests* 11:1–7] to date there have been few attempts to develop strategies and microorganisms for biologically controlling FHB [Stockwell et al., (1997) *Phytopathology* 87(6):S94; Perondi et al, (1996) *Fitopatologia Brasiliera* 21:243–249]. The life cycle of G. zeae suggests that the pathogen is especially susceptible to control using applied microorganisms at anthesis through the soft dough stage of kernel development, when the majority of wheat head infection by G. zeae is generally considered to occur [Andersen, (1948) *Phytopathology* 38:595–611; Arthur, (1981) *Indiana Agric. Exp. Stn. Bull* 36:129–138]; Fernando et al., (1997) *Phytopathology* 87(6):S30 (Abstr.)].

Luz et al. [$5^{th}$ International Congress of Plant Pathology, Abstracts of Papers, p. 348 (1988)] reports in vitro screening in excess of 300 bacteria and yeasts isolated from wheat against *F. graminearum*. Likewise, Perondi et al. [Anais do 2° Simposio de Controle Biológico, Brasilia, DF, p. 128 (Abstr., 1990); *Fitopatologia Brasiliera* 21:243–249 (1996)] reported testing microbial strains as possible antagonists against *F. graminearum*. Promising strains selected by the funnel method and tested in greenhouse studies were shown by Luz et al. [*Fitopatologia Brasiliera* 15(3)246–247 (1990)] to diminish the severity of wheat scab between 7 and 31% when compared to the control.

SUMMARY OF THE INVENTION

We have now discovered 4 yeasts and 1 bacterium as being superior antagonists of *F. graminearum*. These antagonists suppress FHB in cereals, particularly in wheat and barley. The antagonists were selected from a pool of more than 700 microbial strains obtained from anthers of wheat. Initial selection of specific anther colonists for further study was based on random selection or the ability of a colonist to utilize a compound of potential use in formulating the colonist. Selected microbes were then bioassayed on seed heads of a cereal plant, inoculated with *F. graminearum*, for the ability of the strain to reduce the severity of FHB. The five antagonists selected in this manner were superior in reducing FHB severity in greenhouse and in field trials.

In accordance with this discovery, it is an object of this invention to provide novel microbial strains that suppress the profusion of *F. graminearum* in seed heads of wheat and barley.

This and other objects of the invention will become readily apparent from the ensuing description.

DEPOSIT OF BIOLOGICAL MATERIAL

Purified cultures of four yeasts and one bacteria identified as being effective antagonists of *F. graminearum* have been deposited on Sep. 7, 1999, in the U.S. Department of Agriculture, Agricultural Research Service Culture Collection in Peoria, Ill., under the terms of the Budapest Treaty. Accession Numbers for these deposits are as follows:

| | | |
|---|---|---|
| OH 71.4 | NRRL Y-30213 | *Torula aurea* |
| OH 72.4 | NRRL Y-30214 | Unidentified Yeast |
| OH 131.1 | NRRL B-30212 | Bacillus sp. |
| OH 181.1 | NRRL Y-30215 | Torula sp. |
| OH 182.9 | NRRL Y-30216 | *Cryptococcus nodaensis* |

DETAILED DESCRIPTION OF THE INVENTION

For purposes of this invention it is understood that the use of term "Fusarium" is intended to include both the sexual (teleomorphic) stage of this organism and also the asexual (anamorphic) stage, also referred to as the perfect and imperfect fungal stages, respectively. For example, the anamorphic stage of *Gibbereblla zeae* is known as *Fusarium graminearum*, the causative agent of FHB. This disease results when the flower or seed head becomes inoculated with conidia produced by the imperfect form OR ascospores produced by the perfect form of this fungus.

The expression "superior antagonist" used herein in reference to a microorganism is intended to mean that the subject strain exhibits a degree of inhibition of Fusarium-induced head blight exceeding, at a statistically significant level, that of an untreated control.

The term "cereal" as used herein is intended to refer to any cereal species that is normally susceptible to FHB. Cereals reported to be susceptible include wheat, barley, oats, and triticale, though wheat and barley are the two crops in which this disease presents a significant economic problem. Tests in the Examples, below, with one variety of hard red spring wheat, two varieties of soft red winter wheat and one variety of durum wheat demonstrate that antagonist strains of this invention are efficacious in reducing FHB on all these types and varieties of wheat. Any of these cereals may be target species for FHB control.

*F. graminearum* primarily infects the heads (flower heads, seed heads, or seed spikes) of cereal plants from the time of flowering through the soft dough stage of head development. Germinated conidia or ascospores of *F. graminearum* penetrate through anthers and associated tissues to initiate infection of the host and the development of symptoms of FHB.

This invention emanated from the postulation that some of the microorganisms present on (and opportunistically colonizing) cereal anthers may be effective in biologically controlling FHB. Though it is likely that some or all of these same organisms would be present in the head after dehiscence of the anthers, it is considered preferred to collect samples from anthers prior to dehiscence in order to maximize the possibility that a given colonist in the sample is instrumental in the biocontrol of *F. graminearum*. Samples may be subjected to immediate isolation, or alternatively may be frozen in 10% glycerol or the like until use.

Strains may be obtained from the collected anther samples by conventional methods as known in the art. Aqueous or glycerol suspensions of the samples are preferably mixed under conditions of shear to liberate the microorganisms from anther surfaces. Suspensions containing the microorganisms are then serially diluted onto suitable media. Malt extract agar and Tryptic soy broth are exemplary media for use in preferentially isolating yeasts and bacteria, respectively. Corn steep liquor (CSL) medium represents a general purpose isolation medium composed of inexpensive nutrient sources. Microorganisms isolated from CSL would, by the fact that they grew on this medium, be preselected as likely to be amenable to production on a medium that is economically feasible for commercial producers of a prospective biological control product.

Candidate organisms are passed through a plant bioassay in which cells of the microbial strain are introduced to a cereal plant seed head inoculated with conidia of *F. graminearum*. Typically, the *F. graminearum* will be produced on a solidified growth medium and the level of harvested inoculum should be on the order of about $10^4$–$10^6$ conidia/ml, preferably about $10^5$ conidia/ml of aqueous suspension. The cells of candidate antagonist in medium or a suitable buffer are introduced at a level of approximately $10^7$–$10^8$ cfu/ml. In one embodiment of the invention, the conidia of *F. graminearum* and cells of the test strain are combined in a weak phosphate buffer and approximately 10 μL of the suspension are used to inoculate the plant seed head. The plants are then cultivated under conditions of near 100% relative humidity conducive to infection by the fungus for a period of about 3 days. After a period of time sufficient for noticeable development of the disease (usually at least about 2 weeks post inoculation), microbes used to treat seed heads that do not develop visible symptoms of FHB are selected for subsequent evaluation.

Organisms selected in the plant bioassay described above are optionally subjected to a second, more highly replicated plant seed head bioassay similar to the first. The organisms are again grown on a suitable medium until sufficiently expanded for use in the bioassay. However, in this second plant bioassay, it is preferable to grow the strains in liquid culture since this practice is widely used in industry and, antagonists must show bioefficacy when grown under liquid culture conditions. Colonized broth containing cells of individual strains and a conidial suspension of *F. graminearum* are used to inoculate seed heads as previously described. The cells and conidial suspension may be precombined prior to inoculation. As in the first plant bioassay, microbes used to treat seed heads that do not develop visible symptoms of FHB are selected as candidate antagonists.

Confirmation of antagonist efficacy in controlling *F. graminearum* can be made in scaled-up greenhouse studies or in field studies in which flowering plants are treated with cells of the test strains, before, during, or after inoculation with conidia of *F. graminearum*. The plant treatment can be conducted in the same manner as a bona fide field application as described in more detail in Examples 7–9, below.

The aforementioned method was used to isolate and identify five strains of FHB antagonist: OH 71.4 (NRRL Y-30213), *Torula aurea*; OH 72.4 (NRRL Y-30214), an unidentified yeast; OH 131.1 (NRRL B-30212), Bacillus sp.; OH 181.1 (NRRL Y-30215), Torula sp.; and OH 182.9 (NRRL Y-30216), *Cryptococcus nodaensis*. OH 181.1 is considered to be a new species of Torula.

Optimal conditions for the cultivation of antagonists of the invention will, of course, depend upon the particular strain. However, by virtue of the conditions applied in the selection process and general requirements of most microorganisms, a person of ordinary skill in the art would be able to determine essential nutrients and conditions.

The antagonists would typically be grown in aerobic liquid cultures on media which contain sources of carbon, nitrogen, and inorganic salts assimilable by the microorganism and supportive of efficient cell growth. Preferred carbon sources are hexoses such as glucose, but other assimilable sources such as amino acids, may be substituted. Many inorganic and proteinaceous materials may be used as nitrogen sources in the growth process. Preferred nitrogen sources are amino acids and urea but others include gaseous ammonia, inorganic salts of nitrate and ammonium, vitamins, purines, pyrimidines, yeast extract, beef extract, proteose peptone, soybean meal, hydrolysates of casein, distiller's solubles, and the like. Among the inorganic minerals that can be incorporated into the nutrient medium are the customary salts capable of yielding calcium, zinc, iron, manganese, magnesium, copper, cobalt, potassium, sodium, molybdate, phosphate, sulfate, chloride, borate, and like ions.

For the organisms of the invention, cell growth can be achieved at temperatures between 1 and 36° C., with the preferred temperature being in the range of 15–30° C. The pH of the nutrient medium can vary between 4 and 9, but the preferred operating range is pH 6–8. ordinarily, maximal cell yield is obtained in 20–72 hours after inoculation.

The antagonists of the invention can be applied by any conventional method to the surfaces of cereal heads. For example, they can be applied as an aqueous spray or dip, as a wettable powder, or as a dust. Formulations designed for these modes of application will usually include a suitable liquid or solid carrier together with other adjuvants, such as wetting agents, sticking agents and the like. Starch, polysaccharides, sodium alginate, cellulose, etc. are often used in such formulations as carriers and sticking agents.

The expressions "an effective amount" and "a suppressive amount" are used herein in reference to that quantity of antagonist treatment which is necessary to obtain a reduction in the level of disease relative to that occurring in an untreated control under suitable conditions of treatment as described herein. The actual rate of application of a liquid formulation will usually vary from a minimum of about $1 \times 10^3$ to about $1 \times 10^{10}$ viable cells/ml and preferably from about $1 \times 10^6$ to about $5 \times 10^9$ viable cells/ml. Under most conditions, the strains of the invention described in the examples, below, would be optimally effective at application rates in the range of about $1 \times 10^6$ to $1 \times 10^9$ viable cells/ml, assuming a mode of application which would achieve substantially uniform contact of at least about 50% of the wheat head. If the antagonists are applied as a solid formulation, the rate of application should be controlled to result in a comparable number of viable cells per unit area of cereal head surface as obtained by the aforementioned rates of liquid treatment.

It is envisioned that the temperatures at which the antagonists are effective would range from about 5° C. to about 35° C. The preferred temperature range is 15–30° C., and the optimal range is considered to be 18–28° C.

The antagonists can theoretically be applied to the seed head at any time after the boot stage and before the hard dough stage of cereal development. The cereal head is only susceptible to infection by *F. graminearum* from the onset of flowering (anthesis) through the soft dough stage of kernel development. Thus, the best time to apply the biological control agents would be from the time immediately preceding flowering until as late as the soft dough stage of kernel development. Application of antagonists to heads before flowering would allow antagonists to have colonized wheat head parts prior to the wheat head becoming susceptible to infection. Additionally, antagonists would be well positioned to colonize and protect anthers as they emerge from florets. However, it is expected that the antagonists would still be effective if applied after flowering has begun, but before the hard dough stage of development. Though Example 5, below, demonstrates that delays of 4 h between pathogen and antagonist inoculation did not significantly affect antagonist performance, it is anticipated that longer delays may decrease the effectiveness of the microbial treatment depending on methods of cell formulation and application.

The following examples are intended only to further illustrate the invention and are not intended to limit the scope of the invention which is defined by the claims.

EXAMPLE 1

Isolation and Selection of Microbial Strains that Reduce Fusarium Head Blight Disease Collection of Samples Anthers were collected from flowering wheat plants across Illinois and Ohio, two states that have had recent devastating epidemics due to scab. Anthers were removed from wheat flowers using jewelers forceps and placed in vials containing 10% glycerol held at ~5° C. Vials were then frozen at –80° C. Over 400 anther samples were obtained.

Isolation of Strains

To isolate individual strains of microorganisms from anthers, vials were thawed until the glycerol suspension reached 4° C. Vials were then mixed using a vortex for 30 seconds to liberate microorganisms from anther surfaces. Suspensions containing microorganisms were then serially diluted onto a variety of solidified media (18 g/L agar) including corn steep liquor (CSL) (10 g/L Solulys-AST, 1 g/L yeast extract, 2 g/L $KH_2PO_4$, 2 g/L $K_2HPO_4$, 1 g/L $MgSO_4 \cdot 7H_2O$, 0.1 g/L NaCl, 15 g/L glucose, pH 6.8), malt yeast extract [3.0 g/L yeast extract, 3.0 g/L malt extract, 10 g/L glucose, and 5.0 g/L peptone (Type IV)], and one-fifth strength Tryptic soy (TSA/5, pH 6.8)(Difco, Detroit, Mich.). Strains of microorganisms (total of 738) were purified and preserved in 10% glycerin at –80° C.

Stage 1 Plant Seed Head Bioassay

Initial selection of specific anther colonists for further study was based on random selection or the ability of a colonist to utilize tartaric acid, a compound of potential use in formulating the colonist. A total of 188 randomly selected colonists and 54 colonists that utilized the formulating compound were then tested using a stage 1 plant seed head bioassay.

Two seedlings of hard red spring wheat (cultivar "Norm") per 19 cm diameter pot were grown in air-steam pasteurized (60° C. for 30 minutes) potting mix (Terra-lite Rediearth, W.R. Grace, Cambridge, Mass.) in a growth chamber at 25° C., 14 h light/day (600 $\mu$mol/(m·s) for approximately 8 weeks prior to use in bioassays. Conidial inoculum of *F. graminearum* isolate Z3639 was produced on clarified V-8 juice agar at 25° C., 12 h light/day for 7 days while biomass of each strain of microorganism was produced on TSA/5 by inoculating plates and incubating at 25° C. for 48 h. To initiate the plant bioassay for biocontrol agents, conidia of *F. graminearum* 3639 ($10^5$ conidia/ml) and cells of a microbial strain ($10^{7-108}$ cfu/ml) were combined in a weak phosphate buffer and 10 $\mu$L of the suspension used to inoculate the middle floret of two wheat heads per microbial strain. Inoculated wheat plants were placed in a clear plastic enclosure on greenhouse benches for 72 h to promote high relative humidity. The enclosure was then removed and wheat heads were scored for visual symptoms of FHB 16 days after inoculation. Nine microbes that had been used to treat wheat heads that did not develop visible symptoms of FHB were selected for second stage testing of bioefficacy against FHB. Microbial strains were eliminated from consideration if they did not completely prevent FHB symptom development.

Stage 2 Seed Head Plant Bioassay

For those microbial strains that were selected from the stage 1 plant seed head bioassay, a second stage bioassay was performed by inoculating 16 wheat heads (4 heads per replication; 4 replications/treatment) with each selected microbial strain. Strains were grown in semidefined complete liquid medium (SDCL) in Slininger et al., [(1994), M. H. Ryder et al. (Eds.), pp. 29–32 in Improving Plant Productivity with Rhizopshere Bacteria. 3rd International Workshop on Plant Growth-Promoting Rhizobacteria, Adelaide, S. Australia] at 25° C. for 48 h prior to use in stage 2 bioassays. Colonized broth containing cells of individual strains were combined with a conidial suspension of *F. graminearum* Z3639 and a solution of Tween 80 (wetting agent, Sigma Chemical Co., St. Louis, Mo.) and the middle floret of wheat heads inoculated with 10 μL of the suspension. Final concentrations in the suspension used to inoculate wheat heads were $10^7$–$10^8$ cfu/ml microbial cells, $1\times10^5$ conidia/ml of *F. graminearum* Z3639 and 0.04% Tween 80. A total of 9 microbial strains that showed promise in the stage 1 bioassay were bioassayed for efficacy on multiple wheat heads. Five microbial antagonists showed superior efficacy in reducing FHB severity in the stage 2 seed head plant bioassay (Table I) and are the embodiments of the subject invention.

EXAMPLE 2

Greenhouse Assays of Superior Antagonists Against Three Isolates of *F. graminearum*

Hard red spring wheat cultivar "Norm" was used in all assays. Seedlings were grown two to a pot in pasteurized potting mix in a growth chamber for 8 weeks as described above in Example 1. Inoculum of microbial antagonists (Table I) was grown on TSA/5 agar for 24 h prior. These cells were used to inoculate 50 ml of SDCL medium in 200 ml Erlenmeyer flasks that were then held at 25° C. and 250 rpm in a shaker incubator for 48 h prior to use. Conidia of *F. graminearum* isolates Z3639, DOAM, and Fg-9-96 were produced on CV-8 agar as described above. After 8 weeks, wheat plants were transferred to greenhouse benches for approximately 1 week. At the onset of wheat head flowering, generally by the end of 1 week on greenhouse benches, biocontrol bioassays were initiated. The middle floret of a wheat head was inoculated with 10 μL of an aqueous suspension containing 25% antagonist liquid culture, $1\times10^5$ conidia/ml of *F. graminearum*, 0.04% Tween 80, 0.004% phosphate buffer and 0.019% $MgCl_2$. Antagonists colony forming units utilized were approximately $2\times10^7$ for the four yeast antagonists and $5\times10^8$ cfu/ml for the bacterial antagonist. Inoculated wheat plants were then placed in a plastic enclosure on greenhouse benches for 72 h to promote high relative humidity and free moisture necessary for optimal FHB development. Sixteen days after inoculation, wheat heads were scored for disease severity on a 0 to 100% bleached wheat head scale [Stack et al., (1995) North Dakota State University Extension Service Bulletin PP-1095], and a 0 to 100% disease incidence scale. One-hundred kernel weights were determined after heads had matured. Fully developed kernels in healthy heads will have high 100 kernel weights, while shriveled kernels in heads infected by *F. graminearum* will have lower 100 kernel weights. *F. graminearum* was recovered from randomly selected heads showing symptoms of disease development. There were at least four heads per replication and four replications per treatment. In these and all subsequently described greenhouse experiments, treatments were distributed in a completely randomized design. Differences between treatments were determined using analysis of variance (ANOVA) and means separated from controls using Fisher's protected LSD test. Greenhouse experiments were conducted at least twice. Data from repeated, identical experiments were pooled if treatment by experiment interactions were not significant.

The results are reported in Table II. ANOVA revealed that all of the antagonists reduced the impact of FHB for at least two of the three isolates of *F. graminearum* utilized. Strain OH 182.9 was one of the most effective yeast strains, improving at least one of the disease parameters versus the control of each of the 3 isolates of *F. graminearum*.

EXAMPLE 3

Influence of Two Antagonist Cell Concentrations when Inoculating Wheat Heads with Antagonists Immediately Prior to Pathogen Inoculum Antagonists OH 71.4 and OH 182.9 and *F. graminearum* Z3639 were used in replicated experiments. Inoculum of antagonists and pathogen were prepared as described above in Example 2, as were hard red spring wheat plants of cultivar "Norm". Aqueous suspensions containing 10% or 50% of 48 h antagonist liquid culture, 0.04% Tween 80, 0.004% phosphate buffer and 0.019% $MgCl_2$ concentration were prepared as were similar suspensions that contained $1\times10^5$ conidia/ml of *F. graminearum* Z3639 but not antagonist liquid culture. Bacterial suspensions containing 10% or 50% liquid culture corresponded to approximately $2\times10^8$ and $1\times10^9$ cfu/ml respectively. Yeast suspensions containing 10% or 50% liquid culture corresponded to $1\times10^7$ and $5\times10^7$ cfu/ml, respectively. Wheat heads were sprayed with antagonist suspension until run-off and then immediately sprayed with the conidial suspension. Wheat plants were incubated and scored for disease as described above. There were four heads per replication and four replications per treatment that were distributed in a completely randomized design.

The results are reported in Table III, below. When antagonists were applied immediately prior to conidia of *F. graminearum* Z3639, both antagonists at each dose tested reduced FHB for every category measured (disease severity, disease incidence and 100 kernel weights). The performance of antagonists was approximately equal for the two dose levels utilized. Yeast strain OH 71.4 reduced disease severity by an average of 66%.

EXAMPLE 4

Influence of Two Antagonist Cell Concentrations when Inoculating Wheat Heads with Pathogen Inoculum Immediately Prior to Antagonist Inoculum Antagonists OH 71.4 and OH 182.9 and *F. graminearum* Z3639 were used in replicated experiments. All procedures were identical to those described above in Example 3 except that wheat heads were sprayed with the suspension of pathogen conidia immediately before being sprayed with a suspension of antagonist cells.

The results are reported in Table IV, below. When antagonists were applied immediately after conidia of *F. graminearum* Z3639, both antagonists at each dose tested reduced FHB for every category measured (disease severity, disease incidence and 100 kernel weights). Doses of 50% were slightly more effective in reducing symptoms of FHB. Yeast strain OH 71.4 reduced disease severity by an average of 76%.

EXAMPLE 5

Influence of Two Antagonist Cell Concentrations when Inoculating Wheat Heads with Pathogen Inoculum Four Hours Prior to Antagonist Inoculum Antagonists OH 71.4 and OH 182.9 and *F. graminearum* Z3639 were used in replicated experiments. All procedures were identical to those described above in Example 3 except that wheat heads were sprayed with the suspension of pathogen four hours before being sprayed with a suspension of antagonist cells.

The results are reported in Table V, below. Though the arrival of pathogen inoculum 4 h prior to antagonist inoculum would be expected to have resulted in a significant advantage to the pathogen, both concentrations of antagonists utilized were successful in reducing FHB incited by *F. graminearum* Z3639. Both antagonists significantly reduced disease severity at both antagonist concentrations assayed, and OH 71.4 also significantly reduced the level of disease incidence.

EXAMPLE 6

Use of Microbial Antagonists to Control Fusarium Head Blight on Durum Wheat Cultivar "Renville"

Antagonists OH 71.4 and OH 182.9 and *F. graminearum* Z3639 were used in replicated experiments. Antagonist, pathogen and plant production methods were as described previously in Example 2. At the onset of wheat head flowering, generally by the end of 1 week on greenhouse benches, biocontrol bioassays were initiated. The middle floret of a wheat head was coinoculated with 10 $\mu$L of a aqueous suspension containing 25% antagonist liquid culture, $1\times10^5$ conidia/ml of *F. graminearum*, 0.04% Tween 80, 0.004% phosphate buffer and 0.019% $MgCl_2$. Scoring of wheat for disease symptoms and analysis of data was as described previously.

The results are reported in Table VI, below. Antagonist strain OH 71.4 reduced FHB disease severity. Antagonist strain OH 182.9 reduced disease severity, incidence and increased 100 kernel weight compared to the control. These results confirm that antagonists are effective on more than one type of wheat (durum versus hard red spring wheat).

EXAMPLE 7

Microbial Antagonists' Influence on FHB in a First Year Peoria Field Trial

All antagonists reported in Table I were utilized in a First Year field trial conducted in Peoria, Ill., using the soft red winter wheat cultivar "Pioneer 2545". Antagonists were grown in 500 ml Erlenmeyer flasks containing 200 ml of SDCL at 25° C., 250 rpm for 48 h prior to use. Conidial inoculum of *F. graminearum* Z 3639 was produced as described previously in Example 2. Six treatments were applied to 16 foot long rows of wheat, with four replicate rows per treatment. Wheat was sown in late September and treatments were applied to flowering wheat heads in late May of the following year. Treatment suspensions consisted of 20% antagonist liquid culture, $1\times10^4$ conidia/ml of *F. graminearum,* 0.04% Tween 80, 0.004% phosphate buffer and 0.019% $MgCl_2$. The control consisted of all spray components except the antagonist liquid culture. In addition, naturally occurring inoculum of *F. graminearum* would be expected to contribute to FHB development for all treatments in the field studies. Treatments were applied in a completely randomized block design. Plots were scored for disease severity and incidence after 21 days. Animal damage of plots made the collection of 100 kernel weights impossible. Analysis of variance was applied to all data and means separated using Fisher's protect LSD test ($P\leqq0.05$).

The results are reported in Table VII, below. Reduction in FHB severity and disease incidence was provided by 3 of 5 antagonists tested, despite the fact that relatively low levels of antagonists were used in the field test. Yeast strain OH 71.4 reduced disease severity by 43% and disease incidence by 49%, the greatest level of disease control demonstrated by antagonists in this trial.

EXAMPLE 8

Microbial Antagonists' Influence on FHB in a Second Year Peoria Field Trial

All antagonists reported in Table I were utilized in a Second Year field trial conducted in Peoria, Ill. Two cultivars of wheat were utilized and antagonists were applied at two concentrations. Soft red winter wheat cultivars "Pioneer 2545" (FHB susceptible) and "Freedom" (FHB moderately resistant) were planted in late September. Antagonists were applied at 10% and 50% antagonist liquid culture rates in phosphate buffered suspensions containing wetting agent as described above in Example 3. Control rows were sprayed with similar suspensions without antagonist culture. Antagonists were produced as described above except that 1.5 L of SDCL medium in 2.8 L Fernbach flasks was utilized to grow antagonist cells. Conidial inoculum of *F. graminearum* was not included in the antagonist treatment suspensions.

However, in order to increase the opportunity for FHB development, *F. graminearum* Z3639 colonized corn kernels were scattered throughout the plot (approx. 25 kernels/$m^2$) 2 weeks prior to wheat flowering such that ascospores of *F. graminearum* were being released prior to and during wheat flowering and the application of antagonist treatments. Treatments were applied in a completely randomized block design for each wheat cultivar where 8 ft (2.4 m) rows were a replication and there were 4 replications per treatment. Plots were scored for disease severity and incidence after 21 days and plots harvested to determine 100 kernel weights after 42 days. Analysis of variance was applied to all data and means separated using Fisher's protect LSD test ($P\leqq0.05$).

The results are reported in Table VIII, below. Conditions for disease development and antagonist survival were not favorable during and after flowering as high temperatures (30° C.) were common during this interval in Peoria, Ill. Yet, on "Pioneer 2545", three of the five antagonists reduced FHB at one or both of the concentrations assayed. One hundred kernel weights were closely clustered regardless of the treatment. On cultivar "Freedom", all five antagonists reduced FHB at one or both of the concentrations tested. Especially on cultivar "Freedom", higher yeast cell concentrations tended to provide increased levels of FHB reduction.

EXAMPLE 9

Microbial Antagonists' Influence on FHB in Wooster Field Trial

All antagonists reported in Table I were utilized in a field trial conducted in Wooster, Ohio. Antagonists were applied to the soft red winter wheat cultivar "Pioneer 25451" at 10% and 50% antagonist liquid culture rates in phosphate buffered suspensions containing wetting agent as described above in Example 3. Controls were sprayed with similar suspensions without antagonist culture. Antagonists were produced in, Fernbach flasks as described above and naturally occurring inoculum of *F. graminearum* supplemented by scattering *F. graminearum* Z3639 colonized corn kernels throughout the plot (approx. 40 kernels/$m^2$) 2 weeks prior to wheat flowering such that ascospores of *F. graminearum* were being released prior to and during wheat flowering and the application of antagonist treatments. Treatments were applied in a completely randomized block design where 1 $m^2$ plots made up a replication and there were 6 replications per treatment. Plots were scored for disease severity and incidence after 25 days and plots harvested to determine 100 kernel weights after 45 days. Analysis of variance was applied to all data and means separated using Fisher's protect LSD test ($P \leqq 0.05$).

The results are reported in Table IX, below. Conditions for disease development and antagonist survival were not favorable during and after flowering as high temperatures (30° C.) were common during this interval in Wooster, Ohio. All of the five antagonists reduced FHB at one or both of the concentrations assayed with yeast antagonists OH 71.4 reducing disease severity by as much as 56%. Antagonists OH 131.1, OH 181.1 and OH 182.9 reduced disease severity and disease incidence at both of the antagonist cell concentrations tested.

TABLE I

| | Microbial antagonists of FHB | |
|---|---|---|
| Antagonist Strain | Accession Number | Scientific Name |
| OH 71.4 | NRRL Y-30213 | *Torula aurea* |
| OH 72.4 | NRRL Y-30214 | Unidentified Yeast |
| OH 131.1 | NRRL B-30212 | Bacillus sp. |
| OH 181.1 | NRRL Y-30215 | Torula sp. (new sp.) |
| OH 182.9 | NRRL Y-30216 | *Cryptococcus nodaensis* |

TABLE II

Influence of microbial antagonists on FHB incited by three isolates of *Fusarium graminearum* on hard red spring wheat cultivar "Norm"[a]

| | *F. graminearum* isolate | | | | | | | | |
|---|---|---|---|---|---|---|---|---|---|
| | Z3639 | | | DOAM | | | Fg-9-96 | | |
| Treatment | Disease[b] Severity (%) | Disease Incidence (%) | 100 Kernel wt. (g) | Disease Severity (%) | Disease Incidence (%) | 100 Kernel wt. (g) | Disease Severity (%) | Disease Incidence (%) | 100 Kernel wt. (g) |
| *F. graminearum* | 90 | 95 | 1.5 | 76 | 91 | 1.8 | 54 | 66 | 3.2 |
| OH 71.4 | 78 | 82 | 1.9* | 75 | 87 | 2.0* | 3* | 12* | 4.0* |
| OH 72.4 | 82 | 89 | 1.8 | 73 | 84 | 2.0* | 51 | 56 | 2.8* |
| OH 131.1 | 79 | 89 | 2.1* | 75 | 87 | 1.9 | 26* | 34* | 3.8* |
| OH 181.1 | 82 | 89 | 1.9* | 88 | 91 | 1.7* | 44* | 50 | 4.0* |
| OH 182.9 | 39* | 72* | 3.0* | 69 | 84 | 2.0* | 51 | 65 | 3.5* |

[a]The middle floret of a central spikelet of a wheat head was co-inoculated with 10 μl of a 25% suspension of antagonist liquid culture ($10^6$–$10^8$ cfu/ml) and *F. graminearum* conidia ($1 \times 10^5$ conidia/ml).
[b]Within a column, means followed by an asterisk are significantly different from the *F. graminearum* control ($P \leqq 0.05$).

TABLE III

Influence of two antagonist cell concentrations on FHB when wheat heads were inoculated with antagonist cells immediately prior to inoculation with pathogen conidia[a]

| | 48h antagonist liquid culture at: | | | | | |
|---|---|---|---|---|---|---|
| | 10% | | | 50% | | |
| Treatment | Disease[b] Severity (%) | Disease Incidence (%) | 100 Kernel wt. (g) | Disease Severity (%) | Disease Incidence (%) | 100 Kernel wt. (g) |
| *Fusarium graminearum* | 81 | 94 | 1.7 | 81 | 94 | 1.7 |
| OH 71.4 | 18* | 53* | 2.8* | 37* | 41* | 2.5* |
| OH 182.9 | 60* | 78* | 2.3* | 60* | 75* | 2.3* |

[a]Heads of the hard red spring wheat cultivar "Norm" were first sprayed to run-off with a suspension of antagonist cells containing 10% or 50% of 48h antagonist liquid culture, and then immediately sprayed to run-off with a conidial suspension of *F. graminerium* Z3639 ($1 \times 10^5$ conidia/ml).
[b]Within a column, means followed by an asterisk are significantly different from the *F. graminearum control* ($P \leqq 0.05$).

TABLE IV

Influence of two antagonist cell concentrations on FHB when wheat heads were inoculated with pathogen conidia immediately prior to inoculation with antagonist cells[a]

| | 48h antagonist liquid culture at: | | | | | |
|---|---|---|---|---|---|---|
| | 10% | | | 50% | | |
| Treatment | Disease[b] Severity (%) | Disease Incidence (%) | 100 Kernel wt. (g) | Disease Severity (%) | Disease Incidence (%) | 100 Kernel wt. (g) |
| Fusarium graminearum | 76 | 100 | 1.9 | 76 | 100 | 1.9 |
| OH 71.4 | 26* | 62* | 3.6* | 11* | 41* | 3.0* |
| OH 182.9 | NT[c] | — | — | 33* | 78* | 3.2* |

[a]Heads of the hard red spring wheat cultivar "Norm" were first sprayed to run-off with a conidial suspension of F. graminearum Z3639 ($1 \times 10^5$ conidia/ml) and then immediately sprayed to run-off with a suspension of antagonist cells containing 10% or 50% of 48h antagonist liquid culture.
[b]Within a column, means followed by an asterisk are significantly different from the F. graminearum control ($P \leq 0.05$).
[c]NT = Not tested.

TABLE V

Influence of two antagonist cell concentrations on FHB when wheat heads were inoculated with conidia of Fusarium graminearum Z3639 four hours prior to inoculation with antagonist cells[a]

| | 48h antagonist liquid culture at: | | | |
|---|---|---|---|---|
| | 10% | | 50% | |
| Treatment | Disease[b] Severity (%) | Disease Incidence (%) | Disease Severity (%) | Disease Incidence (%) |
| F. graminearum | 59 | 90 | 59 | 90 |
| OH 71.4 | 26* | 53* | 28* | 75 |
| OH 182.9 | 43* | 75 | 43* | 75 |

[a]Heads of the hard red spring wheat cultivar "Norm" were first sprayed to run-off with a conidial suspension of F. graminearum Z3639 ($1 \times 10^5$ conidia/ml) and then four hours later sprayed to run-off with a suspension of antagonist cells containing 10% or 50% of 48h antagonist liquid culture.
[b]Within a column, means followed by an asterisk are significantly different from the F. graminearum control ($P \leq 0.05$).

TABLE VI

Influence of microbial antagonists on FHB incited by Fusarium graminearum Z3639 on durum wheat cultivar "Renville"[a]

| | 48h antagonist liquid culture at: | | |
|---|---|---|---|
| | 25% | | |
| Treatment | Disease[b] Severity (%) | Disease Incidence (%) | 100 Kernel wt. (g) |
| F. graminearum | 50 | 96 | 1.9 |
| OH 71.4 | 36* | 83 | 1.9 |
| OH 182.9 | 27* | 79* | 2.1* |

[a]The middle floret of a central spikelet of a wheat head was co-inoculated with 10 μl of a 25% suspension of antagonist liquid culture ($10^6$–$10^8$ cfu/ml) and F. graminearum conidia ($1 \times 10^5$ conidia/ml).
[b]Within a column, means followed by an asterisk are significantly different from the F. graminearum control ($P \leq 0.05$).

TABLE VII

Use of microbial antagonists to reduce FHB on soft red winter wheat cultivar "Pioneer 2545" in a first season field trial at Peoria, Illinois[a]

| | 48h antagonist liquid culture at: | |
|---|---|---|
| | 20% | |
| Treatment | Disease[b] Severity (%) | Disease Incidence (%) |
| Fusarium graminearum | 4.6 | 35 |
| OH 71.4 | 2.6* | 18* |
| OH 72.4 | 5.2 | 24* |
| OH 131.1 | 3.0* | 24* |
| OH 181.1 | 4.5 | 30 |
| OH 182.9 | 3.1* | 22* |

[a]Wheat heads were sprayed to run-off with a suspension containing antagonist cells (20% of 48h antagonist liquid culture) and F. graminearum Z3639 conidia ($1 \times 10^4$ conidia/ml).
[b]Within a column, means followed by an asterisk are significantly different from the F. graminearum control ($P \leq 0.05$).

TABLE VIII

Influence of two antagonist cell concentrations on FHB development on soft red winter wheat cultivars "Pioneer 2545" and "Freedom" in a second season field trial at Peoria, Illinois[a]

| | Cultivar "Pioneer 2545" | | | | | | Cultivar "Freedom" | | | | | |
|---|---|---|---|---|---|---|---|---|---|---|---|---|
| | 10% Antagonist | | | 50% Antagonist | | | 10% Antagonist | | | 50% Antagonist | | |
| Treatment | Disease[b] Severity (%) | Disease Incidence (%) | 100 kernel wt. (g) | Disease Severity (%) | Disease Incidence (%) | 100 kernel wt. (g) | Disease Severity (%) | Disease Incidence (%) | 100 kernel wt. (g) | Disease Severity (%) | Disease Incidence (%) | 100 kernel wt. (g) |
| *Fusarium graminearum* | 2.0 | 11.2 | 3.3 | 2.0 | 11.2 | 3.3 | 1.0 | 8.3 | 3.1 | 1.0 | 8.3 | 3.1 |
| OH 71.4 | 1.1 | 8.8 | 3.4 | 0.6* | 6.2* | 3.2* | 0.7 | 5.4 | 3.3 | 0.2* | 2.9* | 3.2 |
| OH 72.4 | 1.5 | 11.2 | 3.4 | 1.1 | 7.5 | 3.2 | 0.6 | 2.1* | 3.0 | 1.0 | 5.0 | 3.3* |
| OH 131.1 | 1.9 | 10.4 | 3.2* | 0.7* | 4.6* | 3.3 | 0.7 | 6.7 | 3.2 | 1.6 | 6.2 | 3.3* |
| OH 181.1 | 1.6 | 9.2 | 3.4 | 2.4 | 9.2 | 3.1* | 0.2* | 2.9* | 3.2 | 0.5 | 3.8* | 3.3* |
| OH 182.9 | 0.9* | 5.4* | 3.4 | 1.6 | 6.7* | 3.4 | 0.3* | 3.3* | 3.2* | 0.6 | 3.8* | 3.0 |

[a]Wheat heads were sprayed to run-off with an antagonistic cell suspension. Naturally occurring inoculum of *F. graminearum* was supplemented with ascospores released from *F. graminearum* Z3639 colonized corn kernels that had been spread across the test plot (≈20 colonized kernels/m$^2$).
[b]Within a column, means followed by an asterisk are significantly different from the *F. graminearum* control (P ≤ 0.05).

TABLE IX

Influence of two antagonist cell concentrations on FHB development on soft red winter wheat cultivar "Pioneer 2545" in a field trial at Wooster, Ohio[a]

| | Cultivar "Pioneer 2545" | | | |
|---|---|---|---|---|
| | 10% Antagonist | | 50% Antagonist | |
| Treatment | Disease[b] Severity (%) | Disease Incidence (%) | Disease Severity (%) | Disease Incidence (%) |
| *Fusarium graminearum* | 11.0 | 34.4 | 11.0 | 34.4 |
| OH 71.4 | 4.8 | 23.1* | 9.6 | 30.6 |
| OH 72.4 | 10.7 | 34.4 | 5.3* | 20.3* |
| OH 131.1 | 6.5* | 25.3* | 5.1* | 22.0* |
| OH 181.1 | 6.7* | 27.8* | 6.3* | 25.3* |
| OH 182.9 | 4.6* | 23.1* | 7.1* | 27.0* |

[a]Wheat heads were sprayed to run-off with an antagonist cell suspension. Naturally occurring inoculum of *F. graminearum* was supplemented with ascospores released from *F. graminearum* Z3639 colonized corn kernels that had been spread across the test plot (≈20 colonized kernels/m$^2$).
[b]Within a column, means followed by an asterisk are significantly different from the *F. graminearum* control (P ≤ 0.05).

We claim:

1. A biologically pure culture selected from the group consisting of *Torula aurea* (NRRL Y-30213), an unidentified yeast (NRRL Y-30214), Torula sp. (NRRL Y-30215), and *Cryptococcus nodaensis* (NRRL Y-30216).

2. A biologically pure culture of claim 1, wherein said culture is *Torula aurea* (NRRL Y-30213).

3. A biologically pure culture of claim 1, wherein said culture is an unidentified yeast (NRRL Y-30214).

4. A biologically pure culture of claim 1, wherein said culture is Torula sp. (NRRL Y-30215).

5. A biologically pure culture of claim 1 wherein said culture is *Cryptococcus nodaensis* (NRRL Y-30216).

6. A method for suppressing Fusarium head blight in a cereal plant comprising applying to a seed head of said plant an effective amount of a microbial antagonist selected from the group consisting of *Torula aurea* (NRRL Y-30213), an unidentified yeast (NRRL Y-30214), Torula sp. (NRRL Y-30215), and *Cryptococcus nodaensis* (NRRL Y-30216).

7. The method of claim 6 wherein said microbial antagonist is applied to the seed head prior to hard dough stage of development.

8. The method of claim 6 wherein said microbial antagonist is applied to the seed head during flowering.

9. The method of claim 6 wherein said microbial antagonist is applied to the seed head prior to flowering.

10. The method of claim 6 wherein said cereal is wheat or barley.

11. The method of claim 6 wherein said cereal is wheat.

* * * * *